(12) United States Patent
Imura

(10) Patent No.: US 7,697,136 B2
(45) Date of Patent: Apr. 13, 2010

(54) REFLECTION CHARACTERISTIC MEASURING APPARATUS, AND METHOD FOR CALIBRATING REFLECTION CHARACTERISTIC MEASURING APPARATUS

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 131 days.

(21) Appl. No.: 12/156,003

(22) Filed: May 29, 2008

(65) Prior Publication Data

US 2008/0297791 A1 Dec. 4, 2008

(30) Foreign Application Priority Data

May 31, 2007 (JP) ............................. 2007-144954

(51) Int. Cl.
*G01J 3/00* (2006.01)
*G01J 3/42* (2006.01)

(52) U.S. Cl. ...................................... 356/326

(58) Field of Classification Search ............... 356/319, 356/326, 328
See application file for complete search history.

(56) References Cited

U.S. PATENT DOCUMENTS 6,088,117 A 7/2000 Imura et al.

FOREIGN PATENT DOCUMENTS

JP 11-072388 3/1999

*Primary Examiner*—F. L Evans
(74) *Attorney, Agent, or Firm*—Brinks Hofer Gilson & Lione

(57) ABSTRACT

In a reflection characteristic measuring apparatus 10 and a method for calibrating the reflection characteristic measuring apparatus, multiple standard spectral characteristics, or multiple calibration data based on the multiple standard spectral characteristics are obtained in advance with corresponding reference values relating to an emission characteristic of a light source 21. An optimum standard spectral characteristic or an optimum calibration data is selected from the multiple standard spectral characteristics or the multiple calibration data obtained. A spectral reflection characteristic of a sample is calculated using the selected standard spectral characteristic or the selected calibration data.

11 Claims, 11 Drawing Sheets

FIG.2

| Ir0 | 400 | 410 | 420 | 430 | ... | 670 | 680 | 690 | 700 |
|---|---|---|---|---|---|---|---|---|---|
| 102 | $C_{1,400}$ | $C_{1,410}$ | $C_{1,420}$ | $C_{1,430}$ | ... | $C_{1,670}$ | $C_{1,680}$ | $C_{1,690}$ | $C_{1,700}$ |
| 101.5 | $C_{2,400}$ | $C_{2,410}$ | $C_{2,420}$ | $C_{2,430}$ | ... | $C_{2,670}$ | $C_{2,680}$ | $C_{2,690}$ | $C_{2,700}$ |
| 101 | $C_{3,400}$ | $C_{3,410}$ | $C_{3,420}$ | $C_{3,430}$ | ... | $C_{3,670}$ | $C_{3,680}$ | $C_{3,690}$ | $C_{3,700}$ |
| 100.5 | $C_{4,400}$ | $C_{4,410}$ | $C_{4,420}$ | $C_{4,430}$ | ... | $C_{4,670}$ | $C_{4,680}$ | $C_{4,690}$ | $C_{4,700}$ |
| 100 | $C_{5,400}$ | $C_{5,410}$ | $C_{5,420}$ | $C_{5,430}$ | ... | $C_{5,670}$ | $C_{5,680}$ | $C_{5,690}$ | $C_{5,700}$ |
| 99.5 | $C_{6,400}$ | $C_{6,410}$ | $C_{6,420}$ | $C_{6,430}$ | ... | $C_{6,670}$ | $C_{6,680}$ | $C_{6,690}$ | $C_{6,700}$ |
| 99 | $C_{7,400}$ | $C_{7,410}$ | $C_{7,420}$ | $C_{7,430}$ | ... | $C_{7,670}$ | $C_{7,680}$ | $C_{7,690}$ | $C_{7,700}$ |

WAVELENGTH ($\lambda$ nm)

FIG.3

| T(s) | 400 | 410 | 420 | 430 | ... | 670 | 680 | 690 | 700 |
|---|---|---|---|---|---|---|---|---|---|
| 1 | $C_{1,400}$ | $C_{1,410}$ | $C_{1,420}$ | $C_{1,430}$ | ... | $C_{1,670}$ | $C_{1,680}$ | $C_{1,690}$ | $C_{1,700}$ |
| 1.5 | $C_{2,400}$ | $C_{2,410}$ | $C_{2,420}$ | $C_{2,430}$ | ... | $C_{2,670}$ | $C_{2,680}$ | $C_{2,690}$ | $C_{2,700}$ |
| 2 | $C_{3,400}$ | $C_{3,410}$ | $C_{3,420}$ | $C_{3,430}$ | ... | $C_{3,670}$ | $C_{3,680}$ | $C_{3,690}$ | $C_{3,700}$ |
| 2.5 | $C_{4,400}$ | $C_{4,410}$ | $C_{4,420}$ | $C_{4,430}$ | ... | $C_{4,670}$ | $C_{4,680}$ | $C_{4,690}$ | $C_{4,700}$ |
| 3 | $C_{5,400}$ | $C_{5,410}$ | $C_{5,420}$ | $C_{5,430}$ | ... | $C_{5,670}$ | $C_{5,680}$ | $C_{5,690}$ | $C_{5,700}$ |
| 3.5 | $C_{6,400}$ | $C_{6,410}$ | $C_{6,420}$ | $C_{6,430}$ | ... | $C_{6,670}$ | $C_{6,680}$ | $C_{6,690}$ | $C_{6,700}$ |
| 4 | $C_{7,400}$ | $C_{7,410}$ | $C_{7,420}$ | $C_{7,430}$ | ... | $C_{7,670}$ | $C_{7,680}$ | $C_{7,690}$ | $C_{7,700}$ |

WAVELENGTH (nm)

REFLECTION CHARACTERISTIC MEASURING APPARATUS, AND METHOD FOR CALIBRATING REFLECTION CHARACTERISTIC MEASURING APPARATUS

This application is based on Japanese Patent Application No. 2007-144954 filed on May 31, 2007, the contents of which are hereby incorporated by reference.

BACKGROUND OF THE INVENTION

1. Field of the Invention

The present invention relates to a reflection characteristic measuring apparatus for measuring a reflection characteristic of a sample, and more particularly to a reflection characteristic measuring apparatus for measuring a reflection characteristic of samples by serially illuminating the samples with illumination light from an incandescent lamp, and a method for calibrating the reflection characteristic measuring apparatus.

2. Description of the Related Art

There is known a conventional reflection characteristic measuring apparatus, e.g. a spectrocolorimeter for use in printed matter, for serially measuring reflection characteristics of printed patches, as shown in FIG. 12. Specifically, in the conventional reflection characteristic measuring apparatus, a sample 903 is illuminated with a light flux 902a from an incandescent lamp 902 which is driven by a driving circuit 901 in a direction of 45° with respect to a normal direction to the sample 903, and a normal direction component 903n in sample reflected light obtained by the illumination is condensed on an objective lens 904 for guiding to a spectral device 905. The spectral device 905 measures a spectral intensity of the normal direction component 903 in the sample reflected light, and transmits spectral intensity data 905a obtained by the measurement to a computation control device 906. The computation control device 906 converts the spectral intensity data 905a into a spectral reflection characteristic by a well-known method, based on spectral intensity data of a standard sample, which has been measured and stored in advance in the similar manner as described above, and a known spectral reflectance factor of the standard sample.

In the case where an incandescent lamp popularly used in the reflection characteristic measuring apparatus is driven by a constant voltage, as shown in FIG. 10, immediately after the incandescent lamp is turned on, the filament temperature indicated by the reference numeral 921 is increased by a rush current, with the result that the emission intensity is instantaneously increased. Then, the emission intensity is gradually reduced, and the incandescent lamp is transited to a normal state as shown by the reference numeral 922. A change in intensity of an emission light flux i.e. a change in emission intensity resulting from an increase in filament temperature differs depending on a wavelength. The emission intensity is changed within several seconds immediately after the lamp is turned on.

FIG. 11 is a diagram showing an example of a change in emission intensity, standard at a peak value of the emission intensity, with respect to 450 nm wavelength, 550 nm wavelength, and 650 nm wavelength of an incandescent lamp. As shown in FIG. 11, the degree of change in emission intensity is increased, as the wavelength is shifted to a short wavelength band. An influence of the change in emission intensity is corrected, as shown in FIG. 12, by using a reference spectral section i.e. a reference spectral device in a reference optical system 907 of the reflection characteristic measuring apparatus, and by acquiring spectral intensity data 907a of illumination light from the incandescent lamp 902 (see e.g. Japanese Unexamined Patent Publication No. Hei 11-72388).

In a reflection characteristic measuring apparatus without a reference optical system, or a reflection characteristic measuring apparatus designed to acquire merely data on the light amount with use of a light sensor as a reference optical system, high-precision measurement cannot be performed, because the emission intensity i.e. the spectral intensity is changed. On the other hand, if a reflection characteristic measuring apparatus is designed in such a manner that the apparatus is required to wait until the emission intensity is transited to a normal state, in other words, until the driving condition of the incandescent lamp is stabilized, to secure precision, a long measurement time may be required.

SUMMARY OF THE INVENTION

In view of the above conventional examples, it is an object of the present invention to provide a reflection characteristic measuring apparatus and a method for calibrating the reflection characteristic measuring apparatus that enable to correct an influence of a change in spectral intensity of illumination light, without using a reference spectral section or an equivalent element.

In a reflection characteristic measuring apparatus and a method for calibrating the reflection characteristic measuring apparatus, multiple standard spectral characteristics, or multiple calibration data based on the multiple standard spectral characteristics are respectively obtained in advance with corresponding reference values relating to an emission characteristic of a light source. An optimum standard spectral characteristic or an optimum calibration data is selected from the multiple standard spectral characteristics or the multiple calibration data. A spectral reflection characteristic of a sample is calculated using the selected standard spectral characteristic or the selected calibration data. Accordingly, the inventive reflection characteristic measuring apparatus and the inventive method for calibrating the reflection characteristic measuring apparatus are advantageous in correcting an influence of a change in spectral intensity of illumination light, without using a reference spectral section or an equivalent element.

These and other objects, features and advantages of the present invention will become more apparent upon reading the following detailed description along with the accompanying drawings.

BRIEF DESCRIPTION OF THE DRAWINGS

FIG. 2 is a diagram showing an example of a calibration factor data table.

FIG. 3 is a diagram showing another example of the calibration factor data table.

FIG. 10 is a graph showing a time-based change in light amount, immediately after an incandescent lamp driven at a constant voltage is turned on.

DESCRIPTION OF THE PREFERRED EMBODIMENTS OF THE INVENTION

First Embodiment

Figure 1:
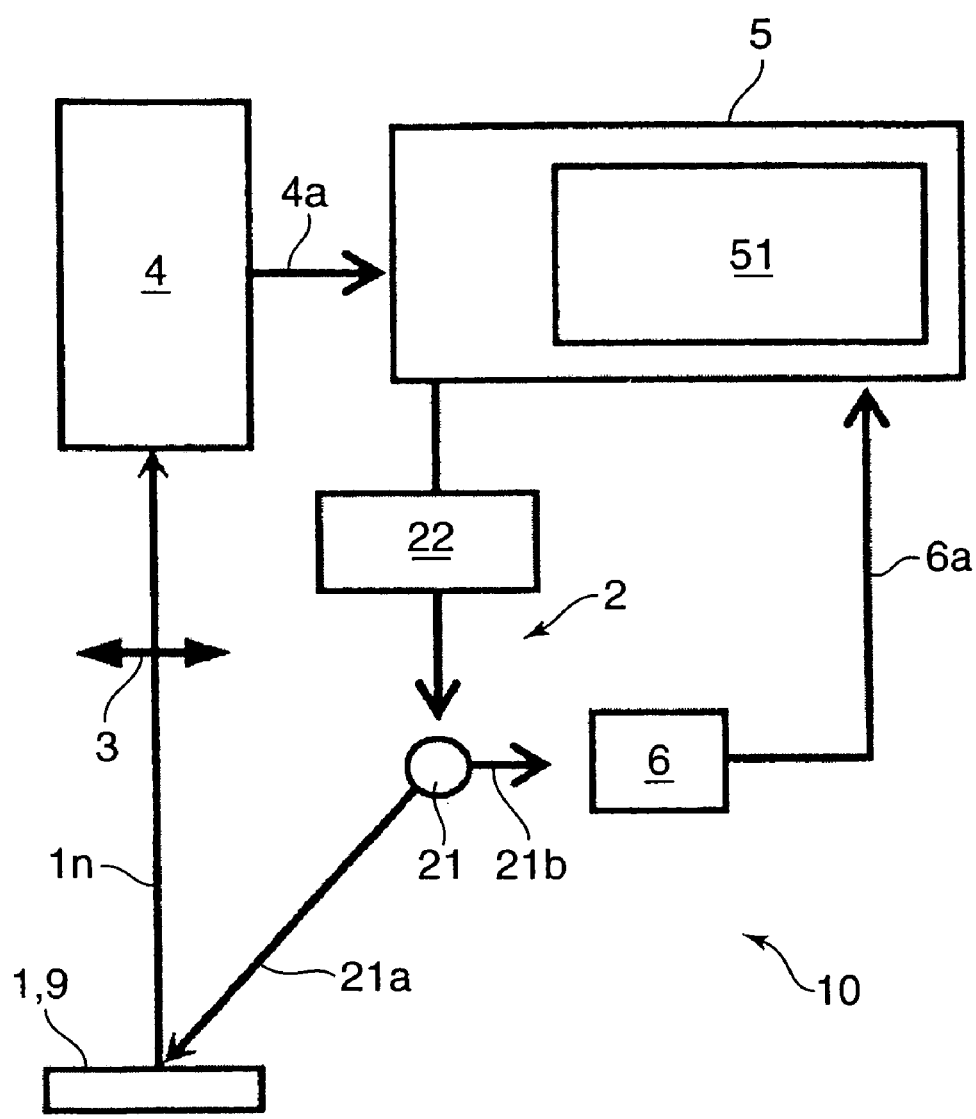
FIG. 1 is a diagram showing an example of an arrangement of a reflection characteristic measuring apparatus in accordance with a first embodiment of the invention.

FIG. 1 is a diagram showing an example of an arrangement of a reflection characteristic measuring apparatus in accordance with the first embodiment of the invention. Referring to FIG. 1, the reflection characteristic measuring apparatus 10 includes an illuminator 2, an objective lens 3, a spectral device 4, a computation control device 5, and a light sensor 6.

The illuminator 2 is adapted to illuminate a sample 1. The illuminator 2 includes e.g. an incandescent lamp 21 as a light source, and a driving circuit 22 for driving the incandescent lamp 21 to turn on the incandescent lamp 21. In this embodiment, the driving circuit 22 is driven at a constant voltage to turn on the incandescent lamp 21.

The objective lens 3 is an optical lens or a lens group, which is operable to receive a normal direction component in, indicating a light component in a direction of normal to a sample surface, in sample reflected light reflected on the sample 1, which is illuminated with light from the incandescent lamp 21, and allow incidence of a light flux of the normal direction component 1n onto the spectral device 4. The spectral device 4 is adapted to measure a spectral intensity of the normal direction component 1n in the sample reflected light.

The computation control device 5 includes e.g. an ROM (Read Only Memory), a RAM (Random Access Memory), and a CPU (Central Processing Unit), and controls overall operations of the reflection characteristic measuring apparatus 10. The computation control device 5 controls operations of the illuminator 2, the spectral device 4, and the light sensor 6, and executes various computation processing relating to calibration in measuring a spectral reflection characteristic of the sample 1, based on output information from the spectral device 4 or the light sensor 6. The computation processing will be described later.

The light sensor 6 is adapted to measure an intensity of illumination light of the incandescent lamp 21 at a time of measuring a reflection characteristic. The computation control device 5 includes a storage 51 for storing table information, which will be described later.

In the reflection characteristic measuring apparatus 10 having the above arrangement, when the incandescent lamp 21 is turned on in response to driving of the driving circuit 22 by the computation control device 5, the incandescent lamp 21 illuminates the sample 1 with a light flux 21a in a direction of about 45° with respect to a normal to the sample 1, in other words, at an incident angle. The normal direction component 1n in the reflected light on the sample 1 illuminated with the illumination light is condensed by the objective lens 3 for guiding to the spectral device 4. The spectral device 4 measures a spectral intensity of the normal direction component in (hereinafter, called as "reflected light component 1n") in the reflected light, and outputs spectral intensity data 4a obtained by the measurement to the computation control device 5. In this embodiment, while the spectral device 4 measures the spectral intensity of the reflected light component in, the light sensor 6 measures the intensity of the illumination light (hereinafter, called as a "reference light flux 21b") from the incandescent lamp 21. The intensity i.e. a reference intensity of the reference light flux 21b obtained by the measurement by the light sensor 6 is outputted to the computation control device 5, as reference data or a reference value 6a, in other words, as a sensor output.

In the reflection characteristic measuring apparatus 10, white calibration is performed prior to the measurement. In the white calibration, a standard sample 9 having a known spectral reflectance factor is measured. In performing the white calibration, the incandescent lamp 21 is turned on by a predetermined method. A spectral intensity I0(λ) (hereinafter, called as a "standard spectral intensity I0(λ)", which corresponds to the spectral intensity data 4a) of reflected light on the standard sample 9 i.e. standard sample reflected light, and a reference intensity R0 (hereinafter, called as a "standard reference intensity R0", which corresponds to the reference data 6a), corresponding to the standard spectral intensity I0(λ), are respectively measured by the spectral device 4 and the light sensor 6 for a predetermined duration immediately after the incandescent lamp 21 is turned on, in other words, a duration from the point of time T0 when a peak or a rapid change of emission intensity immediately after the incandescent lamp 21 is turned on is terminated to a point of time e.g. a point of time Ts when the emission intensity is stabilized, sequentially at a predetermined time interval. The standard reference intensity R0, and a reference intensity R to be described later are also simply called as a "reference value", according to needs.

The series of data on the standard spectral intensity I0(λ) and the standard reference intensity R0 measured in the duration from the point of time T0 to the point of time Ts are transmitted to the computation control device 5, and stored in correlation to each other. More specifically, the computation control device 5 calculates calibration factor data $C_\lambda$ at each wavelength (in this embodiment, in a wavelength range from 400 nm to 700 nm at an interval of 10 nm pitch) based on the following mathematical expression (1), using the transmitted data on the standard spectral intensities I0(λ), and the known spectral reflectance factor W(λ) which is pre-stored in the ROM or the like; and as shown in FIG. 2, stores the calculated calibration factor data $C_\lambda$ into the storage 51, as a calibration factor data table i.e. a lookup table, while correlating the calculated calibration factor data $C_\lambda$ and the standard reference intensity R0 to each other.

$$C_\lambda = W(\lambda)/I0(\lambda) \qquad (1)$$

where the symbol "/" indicates division. The same definition is also applied to the following mathematical expressions.

The symbol Ir0 in the calibration factor data table shown in FIG. 2 corresponds to the standard reference intensity R0. The value 102, 101.5, 101, . . . in the column of Ir0 indicates the light amount of illumination light, i.e. a reference light amount, which has been detected by the light sensor 6, as a current value e.g. in the unit of μA. The data values and the data range of Ir0 are not specifically limited to the example shown in FIG. 2. Each row in the calibration factor data table indicates the calibration factor data $C_\lambda$ at the wavelength 400, 410, 420, . . . at an interval of 10 nm pitch, with respect to the corresponding value of Ir0. For instance, $C_{1,400}, C_{1,410}, C_{1,420}, \ldots$ represents the calibration factor data $C_\lambda$ i.e. a calibration factor data group, at the wavelength 400, 410, 420, ... in the case where Ir0 is 102 mA.

The standard spectral intensities i.e. a series of spectral intensity values obtained by the measurement at the respective points of time in the duration from the point of time T0 to the point of time Ts can be defined as standard spectral characteristics. In this embodiment, each of the standard reference intensities R0, and the standard spectral characteristic obtained at each of the standard reference intensities R0 i.e. at each of the reference values, in other words, the calibration factor data $C_\lambda$ to be obtained based on the standard spectral characteristics, are stored in correlation to each other. The standard spectral characteristics are spectral characteristics corresponding to the respective reference values. Accordingly, the standard spectral characteristics may also be called as "reference spectral characteristics" according to needs.

At the time of measuring the sample 1 (hereinafter, called as "the sample measurement time"), the reflection characteristic measuring apparatus 10 is operable to cause the spectral device 4 and the light sensor 6 to respectively measure a spectral intensity $I(\lambda)$ and a reference intensity R of sample reflected light on the sample 1; cause the computation control device 5 to select calibration factor data $C_\lambda$ i.e. the calibration factor data group, corresponding to a standard reference intensity R0 closest to the reference intensity R at the sample measurement time, from the calibration factor data table stored in the storage 51; and calculate a spectral reflectance factor $Rf(\lambda)$ of the sample 1 based on the following mathematical expression (2), using the selected calibration factor data $C_\lambda$. In other words, the reflection characteristic measuring apparatus 10 is operable to convert the spectral intensity $I(\lambda)$ into the spectral reflectance factor $Rf(\lambda)$.

$$Rf(\lambda)=C_\lambda * I(\lambda) \quad (2)$$

where the symbol "$\lambda$" in $Rf(\lambda)$ or $I(\lambda)$ indicates a wavelength in the range from 400 nm to 700 nm, and the symbol "*" is an operator indicating multiplication. The same definition is also applied to the following mathematical expressions.

The above method is proposed on the premise that the relation between the reference intensity R and the spectral intensity I0 of illumination light, which is obtained after the incandescent lamp 21 is turned on, is unchanged between the white calibration time and the sample measurement time. Normally, a time interval of performing the white calibration is significantly short, as compared with a time required for the characteristic of the incandescent lamp 21 to change. Accordingly, it is conceived that the aforementioned relation is unchanged between the white calibration time and the sample measurement time.

In the reflection characteristic measuring apparatus 10 having the above arrangement, after the incandescent lamp 21 is turned on, measurement can be started with a short wait time, without waiting until the emission intensity is stabilized. Therefore, a time required for measuring a reflection characteristic can be shortened. Also, even in the case where multiple samples e.g. printed patches are sequentially measured, after the incandescent lamp 21 is turned on, optimum calibration factor data $C_\lambda$ can be obtained based on the reference intensity R to be obtained at each of the sample measurement times, and the spectral reflectance factor Rf can be obtained based on the optimum calibration factor data $C_\lambda$. This enables to perform high-speed and high-precision reflection characteristic measurement, while suppressing an influence of fluctuation of a light source.

In the case where the data interval of the standard reference intensities R0 is relatively large, calibration factor data $C_\lambda$ corresponding to the reference intensity R to be obtained at the measurement time may be created by interpolating two calibration factor data $C_\lambda$ corresponding to adjoining two standard reference intensities R0 at each wavelength, based on the relation between the reference intensity R at the measurement time, and the adjoining two standard reference intensities R0. For instance, in the case where the values of Ir0 in the calibration factor data table are 102, 101, 100, ..., there does not exist calibration factor data $C_\lambda$ corresponding to the reference intensity R=101.5 at the measurement time in the calibration factor data table. In this case, the reflection characteristic measuring apparatus 10 may be operable to generate calibration factor data $C_\lambda$ corresponding to the reference intensity R=101.5 for use by linear-interpolating the values of calibration factor data $C_\lambda$ ($C_{1,400}, C_{1,410}, C_{1,420}, \ldots, C_{3,400}, C_{3,410}, C_{3,420}, \ldots$) corresponding to the reference intensity R=101.5, and the adjoining two standard reference intensities R0=102 and 101 at each wavelength. The interpolation is not limited to linear approximation, but may be performed by an interpolation method other than the linear approximation. In the case where interpolation is performed by linear approximation, it is preferable to perform interpolation at a data interval capable of performing linear approximation.

Further alternatively, the reflection characteristic measuring apparatus 10 may be operable to define a value of a current flowing through the incandescent lamp 21 to be obtained in the case where the incandescent lamp 21 is driven at a constant voltage i.e. a filament current value of the incandescent lamp 21, as the reference value of the incandescent lamp 21 in an emission condition, in place of the reference intensity R. Further alternatively, the reflection characteristic measuring apparatus 10 may be operable to define a voltage value to be obtained in the case where the incandescent lamp 21 is driven at a constant current, in other words, a filament voltage value of the incandescent lamp 21, as the reference value, in place of using a condition that the incandescent lamp 21 is driven at a constant voltage. Further alternatively, the reflection characteristic measuring apparatus 10 may include, for instance, a temperature detector e.g. a temperature sensor, and may be operable to define a temperature of the incandescent lamp 21 itself or an ambient temperature of the incandescent lamp 21, which is detected by the temperature detector, e.g. a temperature of a ferrule of the incandescent lamp 21 or a room temperature near the incandescent lamp 21, as the reference value. Further alternatively, the reflection characteristic measuring apparatus 10 may be operable to define combination of some of the reference values, as the reference value. In conclusion, as far as a change or a fluctuation of a spectral intensity of illumination light from the incandescent lamp 21 can be detected, any reference value i.e. a detection parameter may be used.

In the case where the reference value at the sample measurement time is changed over the range of the reference value in the pre-stored calibration factor data table, due to a relatively large change of a temperature such as a room temperature, or a like condition, the reflection characteristic measuring apparatus 10 may be operable to prompt a user to perform white calibration again to create a new calibration factor data table including a reference value at a sample measurement time with some marginal data. In the case where conditions are greatly changed, for instance, in the case where white calibration is performed at a room temperature of 5° C. and sample measurement is performed at a room temperature 30° C., the reference value to be referred to at the sample measurement time is over the data range of Ir0. In this occasion, the reference value is out of the range of the calibration factor data. Considering the above occasion, the reflectance characteristic measuring apparatus 10 may be operable to notify the user of information i.e. a message prompting the user to perform white calibration again. For instance, the reflection characteristic measuring apparatus 10 may include a judging section for judging whether the reference value is over the data range, and a notifying section such as a display section for displaying notification information, or a sound output section for outputting notification information as sounds. For instance, the computation control device 5 may functionally include the judging section for performing judgment i.e. computation for judgment.

The calibration factor data table is not limited to the one shown in FIG. 2, but may include e.g. a calibration factor data table shown in FIG. 3. In the example shown in FIG. 3, a lapse of time after the incandescent lamp 21 is turned on is used, as the standard reference intensity R0. In the calibration factor data table shown in FIG. 3, the lapse of time T(s) is e.g. 1, 1.5, 2, 2.5, . . . , 4 (sec). Calibration factor data $C_\lambda$ corresponding to the lapse of time T(s) is stored in the storage 51.

Second Embodiment

Figure 4:
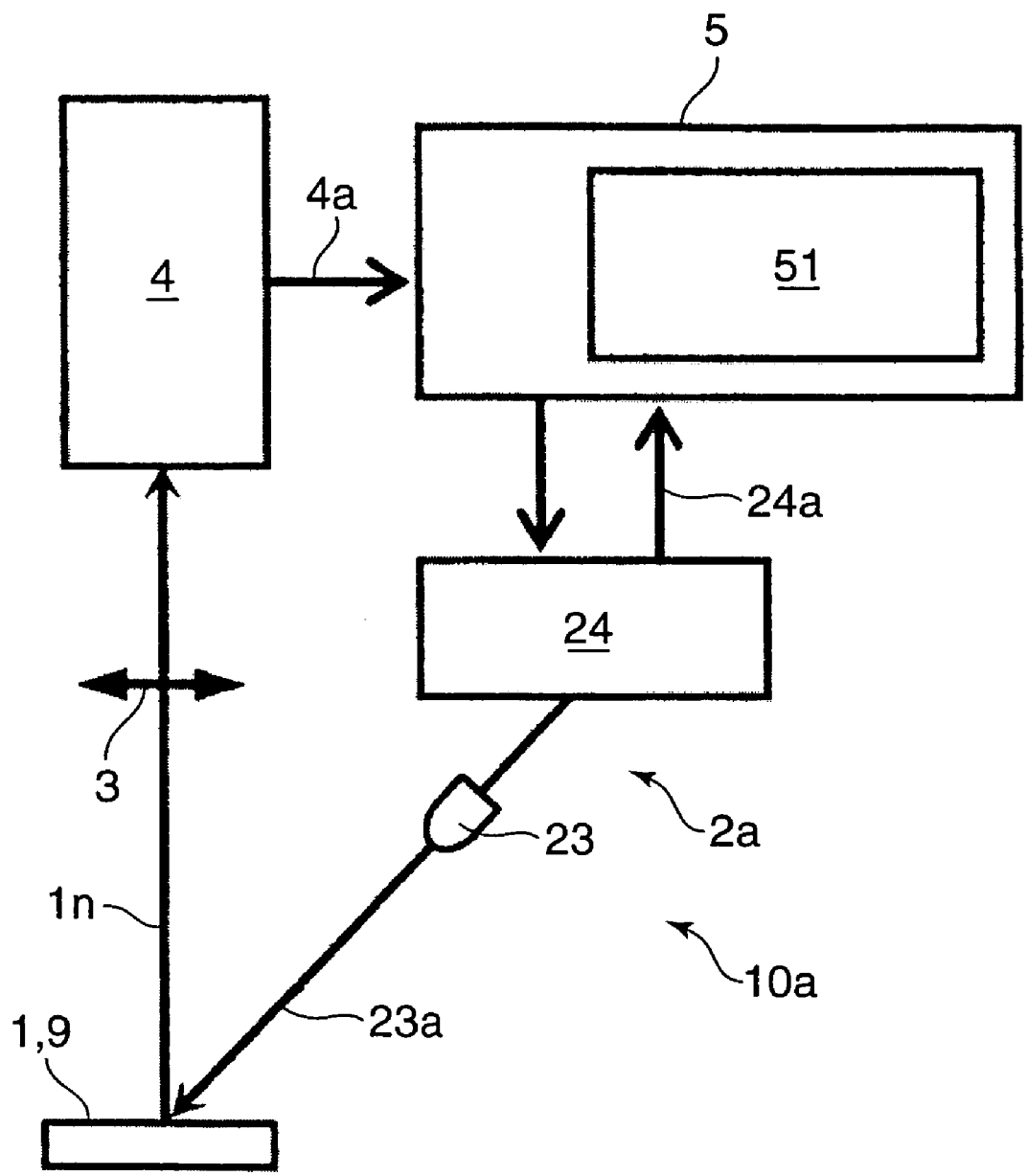
FIG. 4 is a diagram showing an example of an arrangement of a reflection characteristic measuring apparatus in accordance with a second embodiment of the invention.
Figure 6:
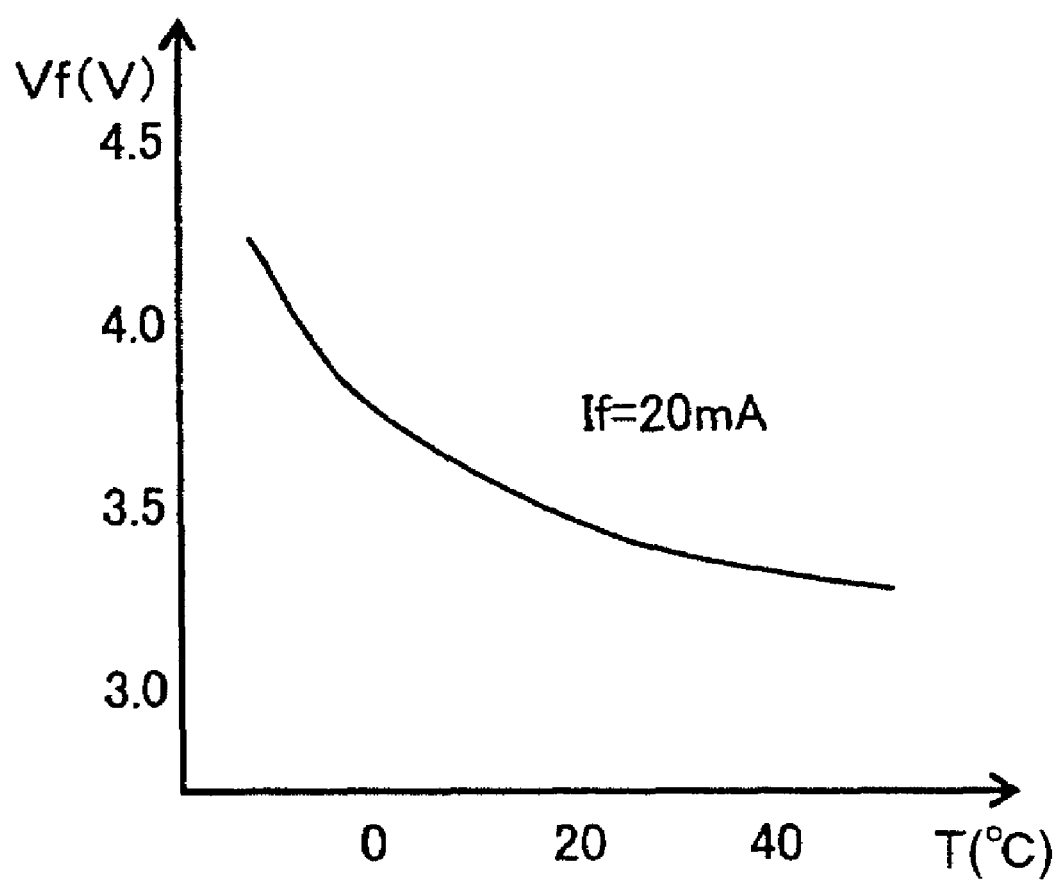
FIG. 6 is a characteristic graph showing a relation between a temperature of the white LED, and a forward voltage.

FIG. 4 is a diagram showing an example of an arrangement of a reflection characteristic measuring apparatus 10a in accordance with the second embodiment of the invention. The reflection characteristic measuring apparatus 10a includes an illuminator 2a incorporated with a white light emitting diode (hereinafter, called as a "white LED") 23, as a light source, in place of the incandescent lamp 21, as an incandescent light source, in the reflection characteristic measuring apparatus 10. In this embodiment, a sample is illuminated with a light flux 23a from the white LED 23 which is driven by a driving circuit 24 at a constant current. A spectral intensity distribution of the white LED 23 primarily depends on a temperature of an LED element i.e. an element temperature. As shown in FIG. 6, there is a relation between a forward voltage Vf of the white LED 23 driven at a constant current (in this embodiment, the constant current is about 20 mA), and the element temperature, depending on individual LEDs. Accordingly, the value of the forward voltage Vf can be defined as a reference value of the white LED 23 in an emission condition. In FIG. 6, the horizontal axis indicates a temperature T(° C.), and the vertical axis indicates a forward voltage Vf(V). The temperature T and the forward voltage Vf in the white LED have such a relation that the value of Vf(V) is reduced, as the value of the temperature T(° C.) is increased.

Figure 5:
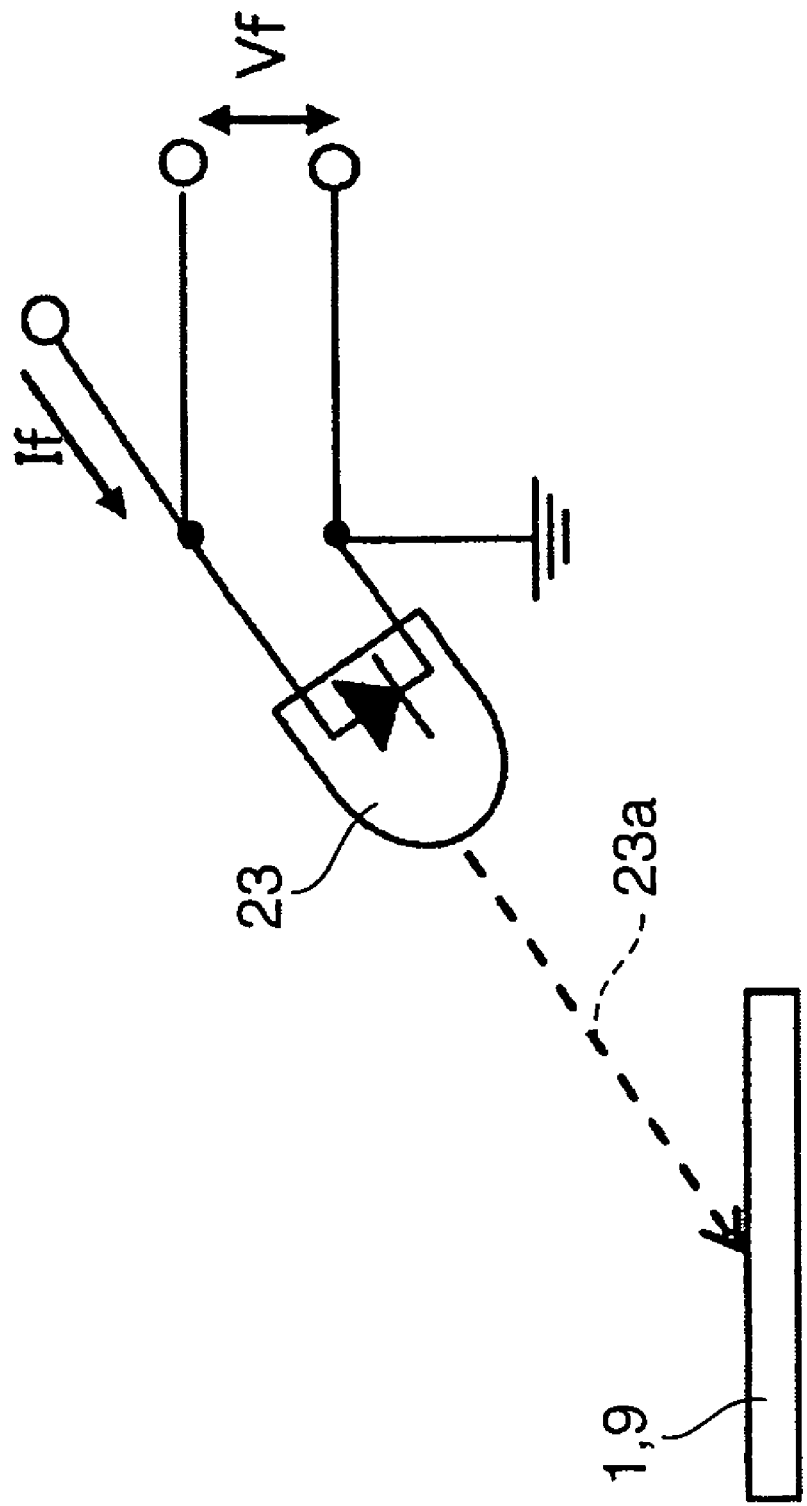
FIG. 5 is an enlarged view of a white LED shown in FIG. 4.

In the above condition, as shown in FIG. 5, which is a partly enlarged view of the white LED 23, the forward voltage Vf of the white LED 23 driven at a constant current If is measured i.e. detected by the driving circuit 24. Data on the detected forward voltage Vf of the white LED 23 is transmitted to a computation control device 5, as reference data 24a. In performing white calibration, the computation control device 5 sequentially acquires a spectral intensity $I0(\lambda)$ (hereinafter, called as a "standard spectral intensity $I0(\lambda)$") of reflected light on a standard sample 9, i.e. standard sample reflected light, and a forward voltage Vf0 (hereinafter, called as a "standard forward voltage Vf0") corresponding to the standard spectral intensity $I0(\lambda)$ in a predetermine duration after the white LED 23 is turned on; and stores the standard spectral intensity $I0(\lambda)$ and the standard forward voltage Vf0 into a storage 51, as a spectral intensity data table, while correlating the standard spectral intensity $I0(\lambda)$ and the standard forward voltage Vf0 to each other. The spectral intensity data table corresponds to the calibration factor data table. In the predetermined duration after the white LED 23 is turned on, the element temperature of the white LED 23 is increased, and the forward voltage is decreased, as the element temperature of the white LED 23 is increased.

At a sample measurement time, the reflection characteristic measuring apparatus 10a is operable to: cause a spectral device 4 and the driving circuit 24 to respectively measure a spectral intensity $I(\lambda)$ of sample reflected light on a sample 1, and a forward voltage Vf; cause the computation control device 5 to select a standard spectral intensity $I0(\lambda)$ corresponding to the forward voltage Vf at the sample measurement time, from the spectral intensity data table stored in the storage 51; and calculate a spectral reflectance factor $Rf(\lambda)$ of the sample 1 based on the following mathematical expression (3), using a known spectral reflectance factor $W(\lambda)$ of the standard sample 9. In this embodiment, the reflection characteristic measuring apparatus 10a is operable to convert the spectral intensity $I(\lambda)$ of the sample 1 into the spectral reflectance factor $Rf(\lambda)$.

$$Rf(\lambda)=W(\lambda)*I(\lambda)/I0(\lambda) \qquad (3)$$

Selecting the standard spectral intensity $I0(\lambda)$ from the spectral intensity data table is substantially equivalent to selecting a value of $W(\lambda)/I0(\lambda)$ in the mathematical expression (3), in other words, selecting the calibration factor data $C_\lambda$ corresponding to the standard reference intensity R0 from the calibration factor data table described in the first embodiment.

In FIG. 4, a sample is illuminated by using the single white LED 23. Alternatively, the reflection characteristic measuring apparatus 10a may include annularly arranged white LEDs, with a normal to a sample surface being defined as an axis of symmetry, to illuminate the sample by the multiple white LEDs. In the modification, the reference value may be the sum or average of forward voltage values of the white LEDs. In the case where all the white LEDs are driven in an identical condition, there is no or less likelihood that a large error may occur, even if the forward voltage of one of the white LEDs is used as the reference value. The spectral intensity distribution, or the characteristic of the white LED including a relation between spectral intensity distribution and temperature may be changed with time. However, a change within a time interval in normal white calibration can be neglected.

Assuming that forward voltages of the white LED 23 driven at two constant currents $I_1$ and $I_2$ are respectively $Vf_1$ and $Vf_2$, the relation between the forward voltage difference $(Vf_1-Vf_2)$, and the element temperature T is represented by the following mathematical expression (4). The forward voltage difference $(Vf_1-Vf_2)$ is proportional to the element temperature T. Accordingly, for instance, the spectral intensity of reflected light and the forward voltage $Vf_1$ in a condition that the white LED 23 is driven at $I_1=20$ mA may be respectively measured; then, for a relatively short duration immediately after the measurement, the forward voltage $Vf_2$ to be obtained in the case where the white LED 23 is driven at $I_2=20$ mA may be measured; and the element temperature T obtained by the following mathematical expression (5) may be defined as the reference value. Further alternatively, the forward voltage difference $(Vf_1-Vf_2)$ itself may be defined as the reference value.

$$Vf_1-Vf_2=(K_b/q)*T*\mathrm{Ln}\,(I_1/I_2) \qquad (4)$$

where $K_b$ indicates a Boltzmann constant, and q indicates an electric charge of electron.

$$T=(Vf_1-Vf_2)/[(K_b/q)*\mathrm{Ln}(I_1/I_2)] \qquad (5)$$

Third Embodiment

Figure 7:
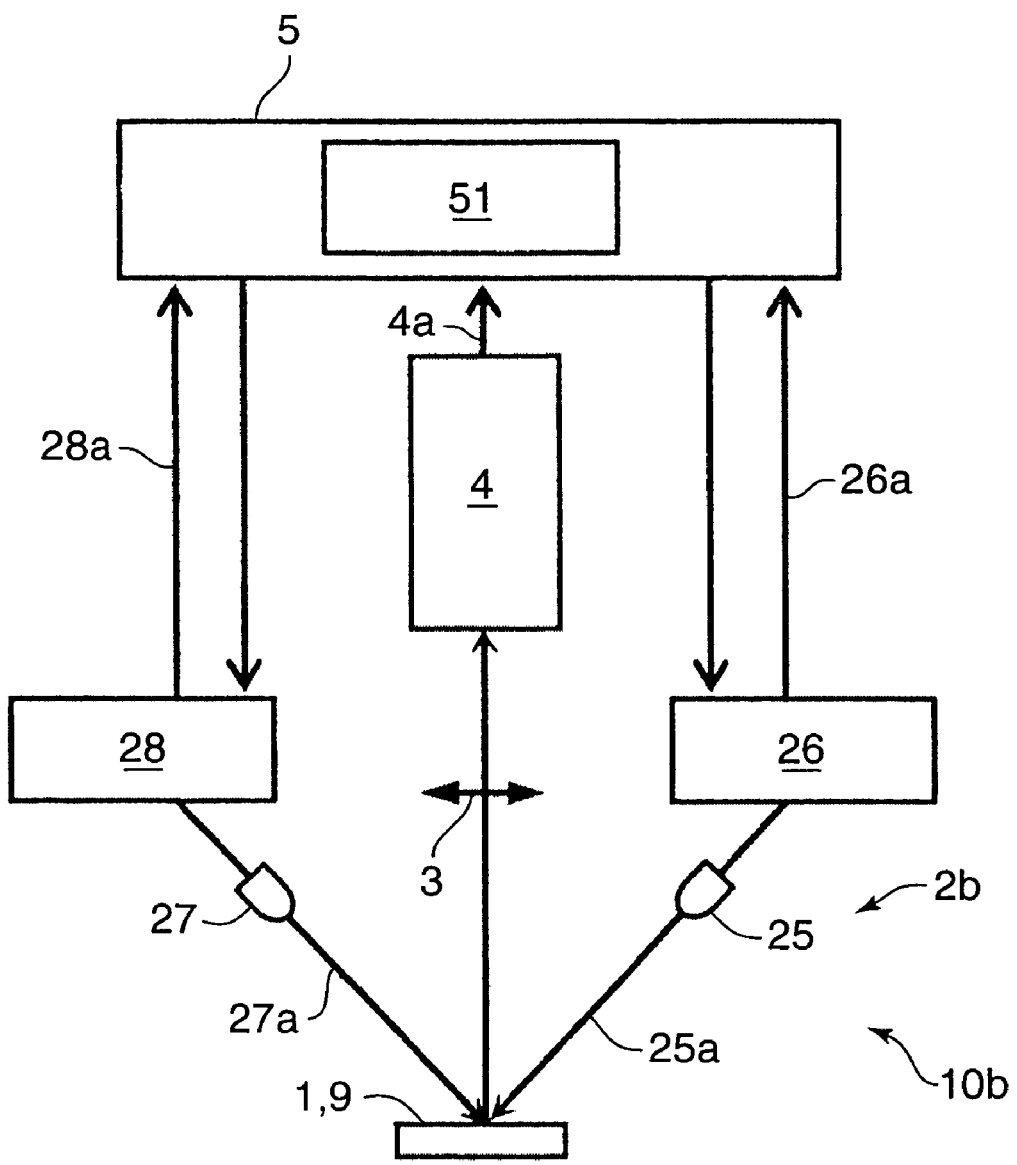
FIG. 7 is a diagram showing an example of an arrangement of a reflection characteristic measuring apparatus in accordance with a third embodiment of the invention.
Figure 8:
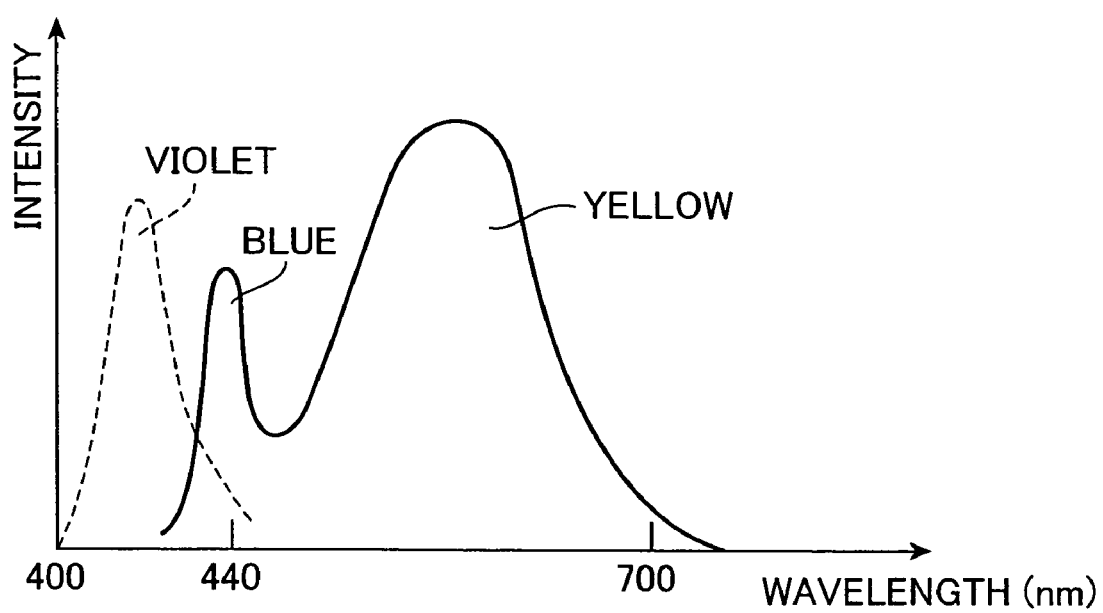
FIG. 8 is a graph showing an example of a spectral intensity distribution of the white LED shown in FIG. 4 and a violet LED.

The reflection characteristic measuring apparatus 10a in the second embodiment includes the illuminator 2a incorporated with the single white LED 23 as a light source. As shown in FIG. 7, a reflection characteristic measuring apparatus 10b in accordance with the third embodiment of the invention includes an illuminator 2b incorporated with two LEDs, as a light source, wherein the two LEDs have spectral intensity distributions different from each other. The two LEDs are, as shown in FIG. 8, for instance, an LED 25 (hereinafter, called as the "white LED 25") having a spectral intensity distribution corresponding to blue light emission, and yellow fluorescent emission excited by the blue light emission; and an LED 27 (hereinafter, called as the "violet LED 27") having a spectral intensity in a wavelength band where the white LED 25 hardly has a spectral intensity, e.g. a wavelength band from 400 to 450 nm.

The white LED 25 and the violet LED 27 are respectively driven by driving circuits 26 and 28 at a constant current. In this embodiment, the white LED 25 and the violet LED 27 have relations different from each other, between a spectral intensity distribution and a forward voltage. Accordingly, white calibration is performed individually with respect to the white LED 25 and the violet LED 27. More specifically, the reflection characteristic measuring apparatus 10b i.e. a computation control device 5 causes the white LED 25 to emit light. Similarly to the arrangement of the second embodiment, a standard spectral intensity $Iw0(\lambda)$ of standard sample reflected light is stored in correlation to a standard forward voltage $Vfw0$, as a spectral intensity data table for white LED. Subsequently, the computation control device 5 causes the violet LED 27 to emit light. Then, a standard spectral intensity $Ip0(\lambda)$ of the standard sample reflected light is stored in correlation to a standard forward voltage $Vfp0$, as a spectral intensity data table for violet LED.

At a sample measurement time, the computation control device 5 is operable to cause the white LED 25 and the violet LED 27 to simultaneously emit light to acquire a spectral intensity $I(\lambda)$ of reflected light on a sample 1; and acquire a forward voltage Vfw (hereinafter, called as a "white LED forward voltage Vfw") of the white LED 25, and a forward voltage Vfp (hereinafter, called as a "violet LED forward voltage Vfp") of the violet LED 27, respectively. The white LED forward voltage Vfw and the violet LED forward voltage Vfp are measured i.e. detected by the driving circuits 26 and 28, and transmitted to the computation control device 5, as reference data 26a and 28a, respectively. The computation control device 5 is operable to select a standard spectral intensity $Iw0(\lambda)$ corresponding to the white LED forward voltage Vfw, and a standard spectral intensity $Ip0(\lambda)$ corresponding to the violet LED forward voltage Vfp, from the spectral intensity data table for white LED, and the spectral intensity data table for violet LED, which are stored in a storage 51, respectively; and calculate a spectral reflectance factor $Rf(\lambda)$ of the sample 1 based on the following mathematical expression (6), using a known spectral reflectance factor $W(\lambda)$ of a standard sample 9. In other words, the computation control device 5 is operable to convert the spectral intensity $I(\lambda)$ of the sample 1 into the spectral reflectance factor $Rf(\lambda)$.

$$Rf(\lambda)=W(\lambda)*I(\lambda)/[Iw0(\lambda)+Ip0(\lambda)] \quad (6)$$

In this embodiment, similarly to the arrangement of the second embodiment, selecting the standard spectral intensity $Iw0(\lambda)$ corresponding to the white LED forward voltage Vfw, and the standard spectral intensity $Ip0(\lambda)$ corresponding to the violet LED forward voltage Vfp, from the spectral intensity data table for white LED and the spectral intensity data table for violet LED, respectively, is substantially equivalent to selecting a value of $W(\lambda)/I0(\lambda)$ in the mathematical expression (3), in other words, selecting the calibration factor data $C_\lambda$ corresponding to the standard reference intensity R0 from the calibration factor data table described in the first embodiment.

In the third embodiment, the reflection characteristic measuring apparatus 10b is operable to cause the white LED 25 and the violet LED 27 to simultaneously emit light to shorten a measurement time. Alternatively, the reflection characteristic measuring apparatus 10b may be operable to cause the white LED 25 and the violet LED 27 to individually emit light. In the modification, after the spectral intensity distribution $Iw(\lambda)$ of sample reflected light on the sample 1 illuminated with illumination light 25a from the white LED 25, and the spectral intensity distribution $Ip(\lambda)$ of sample reflected light on the sample 1 illuminated with illumination light 27a from the violet LED 27 are acquired, $I(\lambda)$, which corresponds to $I(\lambda)$ in the mathematical expression (6), is calculated by summing the spectral intensity distribution $Iw(\lambda)$ and the spectral intensity distribution $Ip(\lambda)$.

In this embodiment, two LEDs are used. Alternatively, three or more LEDs having different spectral intensity distributions may be used. For instance, an LED having a spectral intensity distribution corresponding to green light emission or an infrared light emission may be used, in addition to the white LED and the violet LED. In the modification, a spectral intensity data table corresponding to a forward voltage value may be created with respect to each of the LEDs.

Figure 9:
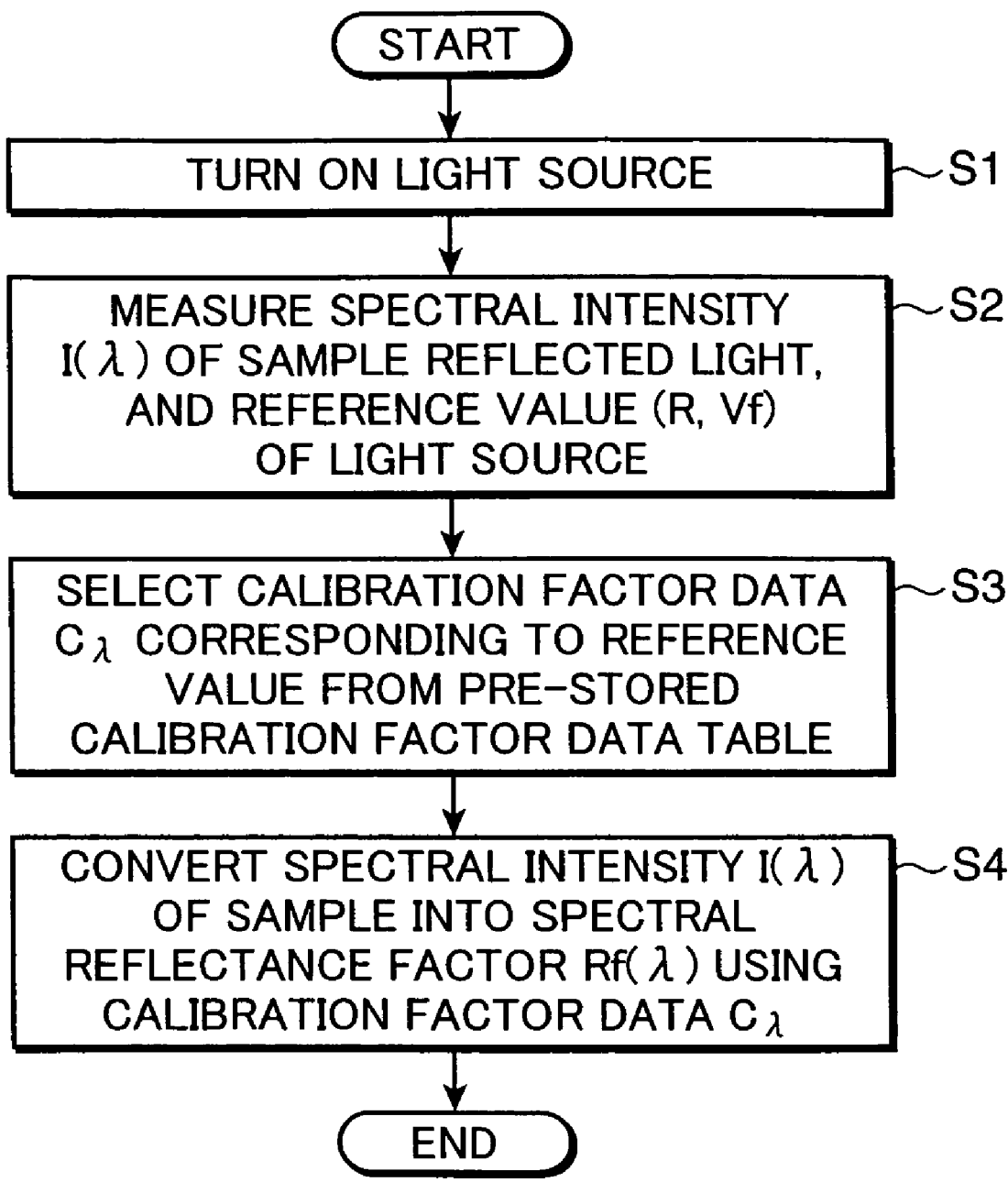
FIG. 9 is a flowchart showing an example of a measurement operation to be performed by the reflection characteristic measuring apparatus in the first, the second, the third embodiment.
Figure 10:
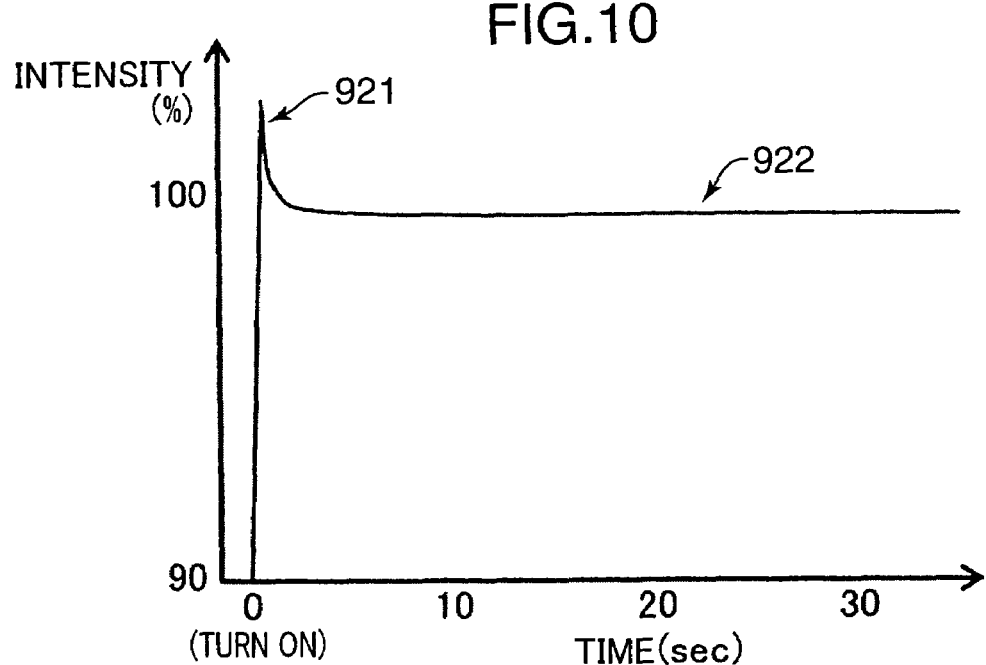

FIG. 9 is a flowchart showing an example of a measurement operation to be performed by the reflection characteristic measuring apparatus 10, 10a, 10b in the first, the second, the third embodiment. First, in Step S1, the light source i.e. the white incandescent lamp 21, the white LED 23, the white LED 25 and the violet LED 27 is turned on to illuminate the sample 1. Then, in Step S2, the spectral intensity $I(\lambda)$ of sample reflected light, and the reference value i.e. the reference value R, Vf, Vfw and Vfp of the light source are respectively measured. In Step S3, the calibration factor data $C_\lambda$ corresponding to the reference value i.e. the standard spectral intensity $I0(\lambda)$, the standard spectral intensities $Iw0(\lambda)$ and $Ip0(\lambda)$, as a reference spectral characteristic, is selected from the calibration factor data table pre-stored in the storage 51 i.e. the spectral intensity data table, the spectral intensity data table for white LED and the spectral intensity data table for violet LED. Then, in Step S4, the spectral intensity $I(\lambda)$ of the sample 1 is converted into the spectral reflectance factor $Rf(\lambda)$ by the mathematical expression (2), (3), (6) using the selected calibration factor data $C_\lambda$. In other words, the spectral reflectance factor $Rf(\lambda)$ of the sample 1 is obtained.

As described above, the reflection characteristic measuring apparatus 10, 10a, 10b in the first, the second, the third embodiment is configured as follows. A light source i.e. the incandescent lamp 21, the white LED 23, the white LED 25 and the ultraviolet LED 27 illuminates a sample. A spectral intensity measuring section i.e. the spectral device 4 measures a spectral intensity of sample reflected light on the sample illuminated with illumination light from the light source. A reference value acquiring section i.e. the light sensor 6, the driving circuit 24, the driving circuits 26 and 28 acquires predetermined reference values relating to an emission characteristic of the light source i.e. the reference data 6a, the reference data 24a, the reference data 26a and 28a. The storage 51, as a storing section, stores standard spectral characteristics, i.e. reference spectral characteristics, respectively obtained in advance with respect to the reference values, or multiple calibration data based on the standard spectral characteristics i.e. the calibration factor data $C_\lambda$, in other words, the calibration factor data table, the spectral intensity data table, the spectral intensity data table for white LED and the spectral intensity data table for violet LED. The computation control device 5 selects a standard spectral characteristic corresponding to the reference value i.e. the reference value R, Vf, Vfw and Vfp acquired at the time of measuring the spectral intensity, or calibration data based on the standard spectral characteristic, in other words, the calibration factor data $C_\lambda$, the standard spectral intensity $I0(\lambda)$, the standard spectral intensities $Iw0(\lambda)$ and $Ip0(\lambda)$, from the standard spectral characteristics or the multiple calibration data stored in the storage 51; and calculate a spectral reflection characteristic i.e. the spectral reflectance factor $Rf(\lambda)$ of the sample, based on the spectral intensity i.e. the spectral intensity $I(\lambda)$ by using the selected standard spectral characteristic or the selected calibration data.

In the above arrangement, even if the emission characteristic of the light source i.e. the spectral intensity is changed, an influence of the change in the spectral intensity can be corrected by a simplified and accurate method, wherein the standard spectral characteristic, or the calibration data based on the standard spectral characteristic, corresponding to the reference value when the spectral intensity is changed, is selected from the pre-acquired data, and a spectral reflection characteristic is properly obtained based on the selected standard spectral characteristic or the selected calibration data, in a significantly short time, as compared with a time required until the light source is stabilized, without using an expensive reference spectral section for acquiring a reference value, and without waiting until the emission condition of the light source is stabilized. This enables to realize a high-speed and high-precision reflection characteristic measuring apparatus at a low cost.

Figure 11:
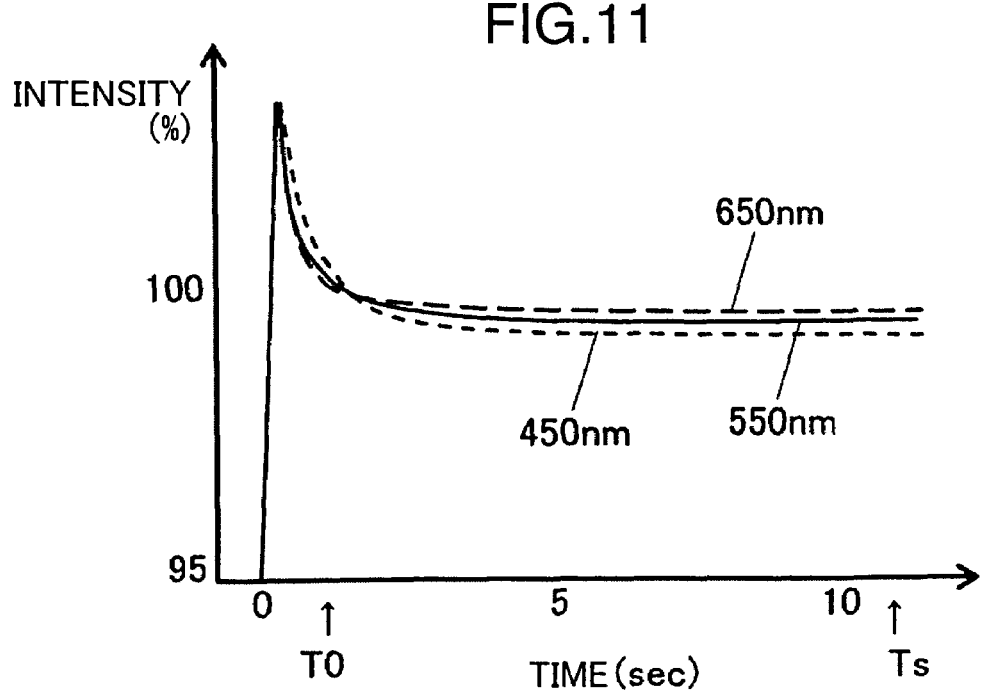
FIG. 11 is a graph for describing a difference of time-based change in light amount depending on a wavelength.
Figure 12:
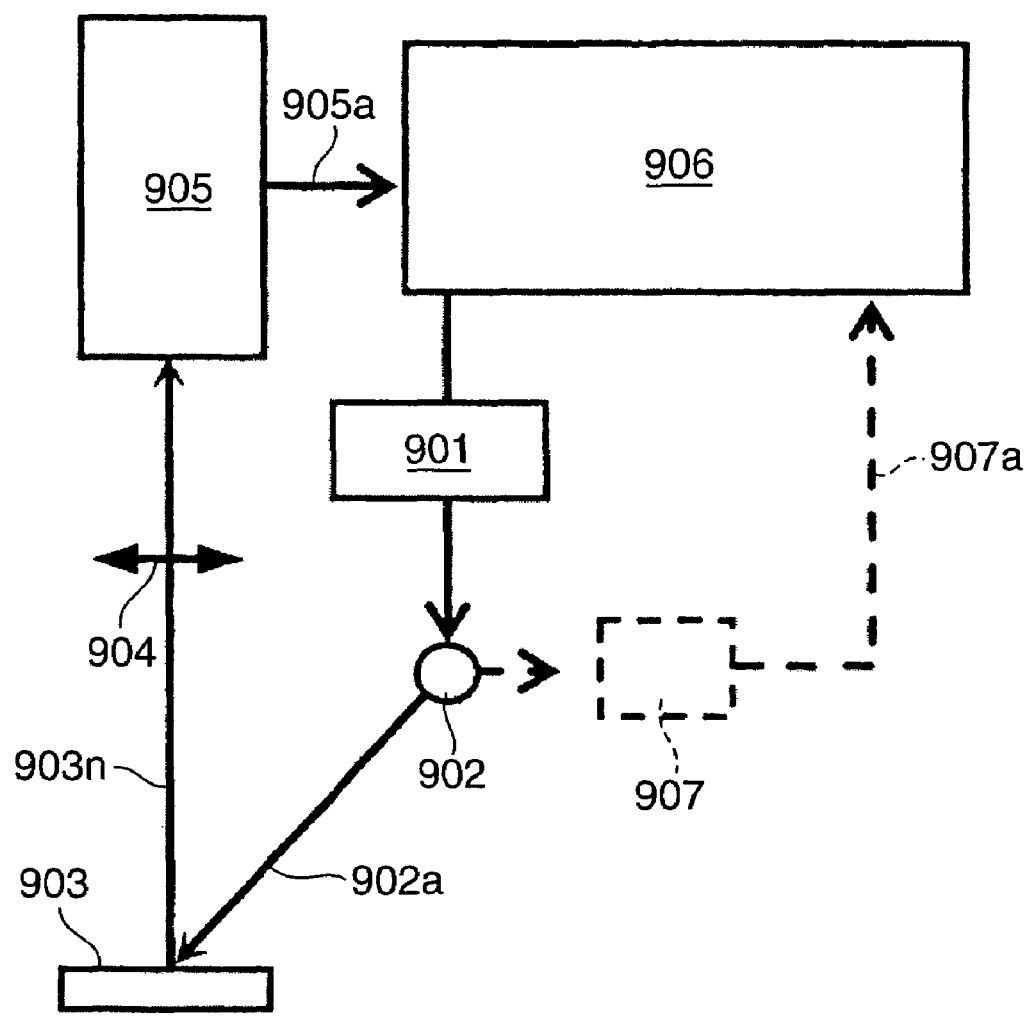
FIG. 12 is a diagram showing an arrangement of a conventional reflection characteristic measuring apparatus.

Preferably, the standard spectral characteristics include spectral intensities, i.e. a series of spectral intensity data, of standard sample reflected light obtained by measuring the standard sample 9 for a predetermined time e.g. a duration from the point of time T0 to the point of time Ts shown in FIG. 11 in a state that the standard sample 9 is continuously illuminated by the light source. This enables to obtain the standard spectral characteristics easily and precisely. Accordingly, a change in the spectral intensity can be corrected with high-precision by using the standard spectral characteristics. Measurement in the predetermined time may be continuous measurement for the duration from the point of time T0 to the point of time Ts shown in FIG. 11, or intermittent measurement, wherein measurement is intermittently performed at a predetermined time interval of e.g. 1 second. The intermittent measurement may be performed several times, with a predetermined time interval between the measurements.

Preferably, the light source includes a light emitting diode to be driven at a constant current i.e. the white LED 23, and the reference acquiring section is operable to acquire a value of the forward voltage Vf to be obtained in the case where the light emitting diode is driven at the constant current If of one or more kinds, as the reference value. This enables to use the light emitting diode with high efficiency (high emission efficiency or low consumption electric power) and high response rate, as the light source, and easily obtain the element temperature T capable of more accurately detecting a change in the spectral intensity, which is directly related to the emission characteristic of the light emitting diode, based on the forward voltage Vf acquired as the reference value. Accordingly, a change in the spectral intensity can be corrected with high-precision by using the element temperature T. Alternatively, high-precision correction can be performed by using the forward voltage Vf itself.

Preferably, the reference value acquiring section is operable to acquire the value of difference $(Vf_1-Vf_2)$ between the forward voltages $Vf_1$ and $Vf_2$ to be obtained in the case where the light emitting diode is driven at two kinds of constant currents $I_1$ and $I_2$. This enables to obtain the element temperature T with high-precision by using a theoretical formula i.e. the mathematical expression (4) or (5), based on the values of the forward voltages $Vf_1$ and $Vf_2$. Accordingly, high-precision correction by using the element temperature T can be performed. Alternatively, high-precision correction can be performed by using the value of difference $(Vf_1-Vf_2)$ between the forward voltages $Vf_1$ and $Vf_2$ itself.

Preferably, the light source includes light emitting diodes of two or more kinds having spectral intensity distributions different from each other, e.g. the white LED 25 and the violet LED 27. The reference value acquiring section is operable to acquire values of forward voltages Vfw and Vfp to be obtained in the case where the light emitting diodes are driven at a constant current of one kind or more, as the reference values, respectively. The storing section is operable to store the standard spectral characteristics and the calibration data to be obtained with respect to each of the light emitting diodes i.e. the spectral intensity data table for white LED and the spectral intensity data table for violet LED. The spectral intensity measuring section is operable to measure the spectral intensity, i.e. the spectral intensity $I(\lambda)$, of the sample reflected light on the sample illuminated by the light emitting diodes of two or more kinds. The computing section is operable to select standard spectral characteristic data respectively corresponding to the reference values of the light emitting diodes acquired at the time of measuring the spectral intensity, i.e. the standard spectral intensities $Iw0(\lambda)$ and $Ip0(\lambda)$, from the standard spectral characteristic data stored in the storing section with respect to each of the light emitting diodes; and calculate a spectral reflection characteristic of the sample based on the spectral intensity of the sample reflected light by using the selected standard spectral characteristic data.

The above arrangement enables to easily obtain illumination light having a spectral intensity in an intended wavelength band by using the light emitting diodes having spectral intensity distributions different from each other, and obtain the spectral reflection characteristic with high-precision by using the standard spectral characteristic data obtained individually with respect to each of the light emitting diodes.

Preferably, the reference value acquiring section includes the light sensor 6 i.e. a photosensitive sensor for detecting a part of a light flux emitted from the light source, and is operable to acquire an output value of the photosensitive sensor, as the reference value. This enables to acquire the reference value with a simplified arrangement, at a low cost, and with high precision.

Preferably, the reference value acquiring section is operable to acquire data on a temperature of the light source or data on an ambient temperature of the light source, as the reference value. This enable to easily acquire the reference value with a simplified arrangement using e.g. a temperature sensor.

Preferably, the reference value acquiring section is operable to acquire data on a lapse of time (see the time T(s) in FIG. 3) after the light source is turned on, as the reference value. This enables to acquire the reference value at a low cost, without the need of providing a dedicated sensor or a like element for acquiring the reference value.

Preferably, the light source includes the incandescent lamp 21 to be driven at a constant voltage or a constant current, and the reference value acquiring section is operable to acquire a value of a filament current or a value of a filament voltage of the incandescent lamp 21, as the reference value. This enable to acquire the reference value at a low cost, without the need of providing a dedicated sensor or a like element for acquiring the reference value.

Preferably, a judging section, i.e. the computation control device 5, is operable to judge whether the reference value acquired at the time of measuring the spectral intensity exceeds the range of the reference values corresponding to the standard spectral characteristics or the calibration data stored in the storing section. In the case where it is judged that the acquired reference value exceeds the range of the reference values corresponding to the standard spectral characteristics or the calibration data stored in the storing section, a notifying section is operable to notify a user of information prompting the user to measure the standard sample again i.e. perform white calibration again for obtaining the standard spectral characteristics, or the multiple calibration data based on the standard spectral characteristics, respectively corresponding to the reference values.

The above arrangement enables to securely alert the user that the acquired reference value greatly exceeds the allowable range, in other words, white calibration re-execution is required. In this arrangement, even if the emission intensity of the light source greatly exceeds the allowable range resulting from a change in room temperature or a like condition, a proper measure can be taken. This enables to prevent erroneous measurement of the spectral reflection characteristic.

According to another aspect of the invention, a method for calibrating a reflection characteristic measuring apparatus adapted to measure a spectral reflection characteristic of a sample by illuminating the sample, comprises: a first step of illuminating a sample by a light source; a second step of measuring a spectral intensity of sample reflected light reflected on the sample illuminated with illumination light from the light source; a third step of acquiring predetermined reference values relating to an emission characteristic of the light source; a fourth step of storing standard spectral characteristics, i.e. the reference spectral characteristics, or calibration data based on the standard spectral characteristics, respectively obtained in advance with respect to the reference values; a fifth step of selecting a standard spectral characteristic, or the calibration data based on the standard spectral characteristic, corresponding to the reference value acquired at the time of measuring the spectral intensity, from the standard spectral characteristics or the calibration data stored in the storing step; and a sixth step of calculating a spectral reflection characteristic of the sample based on the spectral intensity by using the standard spectral characteristic or the calibration data selected in the selecting step.

In the above arrangement, even if the emission characteristic of the light source i.e. the spectral intensity is changed, an influence of the change in the spectral intensity can be corrected by a simplified and accurate method, wherein the standard spectral characteristic, or the calibration data based on the standard spectral characteristic, corresponding to the reference value when the spectral intensity is changed, is selected from the pre-acquired data, and a spectral reflection characteristic is properly obtained based on the selected standard spectral characteristic or the selected calibration data, in a significantly short time, as compared with a time required until the light source is stabilized, without using an expensive reference spectral section for acquiring a reference value, and without waiting until the emission condition of the light source is stabilized. This enables to realize a calibration method capable of high-speed and high-precision reflection characteristic measurement at a low cost.

The specification discloses the aforementioned arrangements. The following is a summary of the primary arrangements of the embodiments.

A reflection characteristic measuring apparatus, according to an aspect of the invention comprises: a light source for illuminating a sample; a spectral intensity measuring section for measuring a spectral intensity of light reflected by the sample illuminated with illumination light from the light source; a reference value acquiring section for acquiring reference values relating to an emission characteristic of the light source; a storing section for storing multiple standard spectral characteristics, or multiple calibration data based on the multiple standard spectral characteristics obtained in advance with corresponding reference values; a selecting section for selecting a standard spectral characteristic, or a calibration data based on the standard spectral characteristic, corresponding to the reference value acquired at the time of measuring the spectral intensity of light reflected by a sample, from the multiple standard spectral characteristics or the multiple calibration data stored in the storing section; and a computing section for calculating a spectral reflection characteristic of the sample based on the spectral intensity using the standard spectral characteristic or the calibration data selected by the selecting section.

A method for calibrating a reflection characteristic measuring apparatus, according to another aspect of the invention, comprises the steps of: illuminating a sample by a light source; measuring a spectral intensity of light reflected by the sample illuminated with illumination light from the light source; acquiring reference values relating to an emission characteristic of the light source; selecting a standard spectral characteristic, or calibration data based on the standard spectral characteristic, corresponding to the reference value acquired in the spectral intensity measuring step, from multiple standard spectral characteristics, or multiple calibration data based on the multiple standard spectral characteristics obtained in advance with corresponding reference values; and calculating a spectral reflection characteristic of the sample based on the spectral intensity using the standard spectral characteristic or the calibration data selected in the selecting step.

In the reflection characteristic measuring apparatus and the calibration method, even if the emission characteristic of the light source i.e. the spectral intensity is changed, an influence of the change in the spectral intensity can be corrected by a simplified and accurate method, wherein the standard spectral characteristic, or the calibration data based on the standard spectral characteristic, corresponding to the reference value when the spectral intensity is changed, is selected from the pre-acquired data, and a spectral reflection characteristic is properly obtained based on the selected standard spectral characteristic or the selected calibration data, in a significantly short time, as compared with a time required until the light source is stabilized, without using an expensive reference spectral section for acquiring a reference value, and without waiting until the emission condition of the light source is stabilized. This enables to realize high-speed and high-precision reflection characteristic measurement at a low cost.

Preferably, the multiple standard spectral characteristics may include multiple spectral intensities of light reflected by a standard sample obtained by continuously measuring light reflected by the standard sample for a predetermined time after the light source is turned on.

In the above arrangement, the standard spectral characteristics can be easily and precisely obtained. Accordingly, a change in the spectral intensity can be corrected with high-precision by using the standard spectral characteristics.

Preferably the light source may include a light emitting diode driven by a constant current, and the reference value acquiring section may be operable to acquire a forward voltage of the light emitting diode driven by one or more constant currents, as the reference value.

The above arrangement enables to use a light emitting diode with high efficiency (high emission efficiency or low consumption electric power) and high response rate, as the light source, and easily obtain an element temperature capable of more accurately detecting a change in the spectral intensity, which is directly related to the emission characteristic of the light emitting diode, based on the forward voltage acquired as the reference value. Accordingly, a change in the spectral intensity can be corrected with high-precision by using the element temperature. Alternatively, high-precision correction may be performed by using the forward voltage itself.

Preferably, the reference value acquiring section may be operable to acquire a difference between the forward voltages of the light emitting diode driven by two different constant currents.

The above arrangement enables to obtain the element temperature with high-precision by using a theoretical formula, based on the values of the forward voltages. Accordingly, high-precision correction by using the element temperature can be performed. Alternatively, high-precision correction may be performed by using the value of difference between the forward voltages itself.

Preferably, the light source may include light emitting diodes of two or more kinds having spectral intensity distributions different from each other. The reference value acquiring section may be operable to acquire a forward voltage of the light emitting diodes driven by one or more constant currents. The storing section may be operable to store the multiple standard spectral characteristics with corresponding forward voltages obtained with respect to each of the light emitting diodes. The spectral intensity measuring section may be operable to measure the spectral intensity of light reflected by the sample illuminated by the light emitting diodes of two or more kinds. The selecting section may be operable to select a standard spectral characteristic data respectively corresponding to a forward voltage of each of the light emitting diodes acquired at the time of measuring the spectral intensity of light reflected by a sample, from the standard spectral characteristic data stored in the storing section with respect to each of the light emitting diodes. The computing section may be operable to calculate the spectral reflection characteristic of the sample based on the spectral intensity of the reflected light using the standard spectral characteristic data selected by the selecting section.

The above arrangement enables to easily obtain illumination light having a spectral intensity in an intended wavelength band by using the light emitting diodes having spectral intensity distributions different from each other; and obtain the spectral reflection characteristic with high-precision by using the standard spectral characteristic data obtained individually with respect to each of the light emitting diodes.

Preferably, the reference value acquiring section may include a photosensitive sensor for detecting a part of a light flux emitted from the light source, and may be operable to acquire an output of the photosensitive sensor, as the reference value.

The above arrangement enables to acquire the reference value with a simplified arrangement, at a low cost, and with high precision.

Preferably, the reference value acquiring section may be operable to acquire a temperature of the light source or an ambient temperature of the light source, as the reference value.

The above arrangement enables to easily acquire the reference value with a simplified arrangement using e.g. a temperature sensor.

Preferably, the reference value acquiring section may be operable to acquire an elapsed time after the light source is turned on, as the reference value.

The above arrangement enables to acquire the reference value at a low cost, without the need of providing a dedicated sensor or a like element for acquiring the reference value.

Preferably, the light source may include an incandescent lamp driven by a constant voltage or a constant current, and the reference value acquiring section may be operable to acquire a filament current or a filament voltage of the incandescent lamp driven by a constant voltage or a constant current respectively, as the reference value.

The above arrangement enables to acquire the reference value at a low cost, without the need of providing a dedicated sensor or a like element for acquiring the reference value.

Preferably, the reflection characteristic measuring apparatus may further comprise: a judging section for judging whether the reference value acquired at the time of measuring the spectral intensity exceeds a range of the reference values corresponding to the standard spectral characteristics or the calibration data stored in the storing section; and a notifying section for notifying a user of information prompting the user to measure the standard sample again for adding the standard spectral characteristics, or the multiple calibration data based on the standard spectral characteristics with corresponding reference values, in the case where the acquired reference value exceeds the range of the reference values corresponding to the standard spectral characteristic or the calibration data stored in the storing section.

The above arrangement enables to securely alert the user that the acquired reference value greatly exceeds the allowable range, in other words, white calibration re-execution is required. In this arrangement, even if the emission intensity of the light source greatly exceeds the allowable range resulting from a change in room temperature or a like condition, a proper measure can be taken. This enables to prevent erroneous measurement of the spectral reflection characteristic.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A reflection characteristic measuring apparatus, comprising:
    a light source for illuminating a sample;
    a spectral intensity measuring section for measuring a spectral intensity of light reflected by the sample illuminated with illumination light from the light source;
    a reference value acquiring section for acquiring reference values relating to an emission characteristic of the light source;
    a storing section for storing multiple standard spectral characteristics, or multiple calibration data based on the multiple standard spectral characteristics, obtained in advance with corresponding reference values;

a selecting section for selecting a standard spectral characteristic, or a calibration data based on the standard spectral characteristic, corresponding to a reference value acquired at the time of measuring the spectral intensity of light reflected by a sample, from the multiple standard spectral characteristics or the multiple calibration data stored in the storing section; and a computing section for calculating a spectral reflection characteristic of the sample based on the spectral intensity using the standard spectral characteristic or the calibration data selected by the selecting section.

2. The reflection characteristic measuring apparatus according to claim 1, wherein the multiple standard spectral characteristics include multiple spectral intensities of light reflected by a standard sample obtained by continuously measuring light reflected by the standard sample for a predetermined time after the light source is turned on.

3. The reflection characteristic measuring apparatus according to claim 1, wherein the light source includes a light emitting diode driven by a constant current, and the reference value acquiring section is operable to acquire a forward voltage of the light emitting diode driven by one or more constant currents, as the reference value.

4. The reflection characteristic measuring apparatus according to claim 3, wherein the reference value acquiring section is operable to acquire a difference between the forward voltages of the light emitting diode driven by two different constant currents.

5. The reflection characteristic measuring apparatus according to claim 1, wherein the light source includes light emitting diodes of two or more kinds having spectral intensity distributions different from each other, the reference value acquiring section is operable to acquire a forward voltage of each of the light emitting diodes driven by one or more constant currents, the storing section is operable to store the multiple standard spectral characteristics obtained with corresponding forward voltages with respect to each of the light emitting diodes, the spectral intensity measuring section is operable to measure the spectral intensity of light reflected by the sample illuminated by the light emitting diodes of two or more kinds, the selecting section is operable to select a standard spectral characteristic data respectively corresponding to a forward voltage of each of the light emitting diodes acquired at the time of measuring the spectral intensity of light reflected by a sample, from the standard spectral characteristic data stored in the storing section with respect to each of the light emitting diodes, and the computing section is operable to calculate the spectral reflection characteristic of the sample based on the spectral intensity of the reflected light using the standard spectral characteristic data selected by the selecting section.

6. The reflection characteristic measuring apparatus according to claim 1, wherein the reference value acquiring section includes a photosensitive sensor for detecting a part of a light flux emitted from the light source, and is operable to acquire an output of the photosensitive sensor, as the reference value.

7. The reflection characteristic measuring apparatus according to claim 1, wherein the reference value acquiring section is operable to acquire a temperature of the light source or an ambient temperature of the light source, as the reference value.

8. The reflection characteristic measuring apparatus according to claim 1, wherein the reference value acquiring section is operable to acquire an elapsed time after the light source is turned on, as the reference value.

9. The reflection characteristic measuring apparatus according to claim 1, wherein the light source includes an incandescent lamp driven by a constant voltage or a constant current, and the reference value acquiring section is operable to acquire a filament current or a filament voltage of the incandescent lamp driven by a constant voltage or a constant current respectively, as the reference value.

10. The reflection characteristic measuring apparatus according to claim 2, further comprising:

a judging section for judging whether the reference value acquired at the time of measuring the spectral intensity exceeds a range of the reference values corresponding to the standard spectral characteristics or the calibration data stored in the storing section; and a notifying section for notifying a user of information prompting the user to measure the standard sample again for adding the standard spectral characteristics, or the multiple calibration data based on the standard spectral characteristics with corresponding reference values, in the case where the acquired reference value exceeds the range of the reference values corresponding to the standard spectral characteristics or the calibration data stored in the storing section.

11. A method for calibrating a reflection characteristic measuring apparatus, comprising the steps of:

illuminating a sample by a light source;

measuring a spectral intensity of light reflected by the sample illuminated with illumination light from the light source;

acquiring reference values relating to an emission characteristic of the light source;

selecting a standard spectral characteristic, or calibration data based on the standard spectral characteristic, corresponding to the reference value acquired in the spectral intensity measuring step, from multiple standard spectral characteristics, or multiple calibration data based on the multiple standard spectral characteristics obtained in advance with corresponding reference values; and calculating a spectral reflection characteristic of the sample based on the spectral intensity using the standard spectral characteristic or the calibration data selected in the selecting step.

* * * * *